(12) United States Patent
Lan et al.

(10) Patent No.: US 11,534,510 B2
(45) Date of Patent: Dec. 27, 2022

(54) UV GERMICIDAL PANEL LIGHT

(71) Applicant: SHENZHEN GUANKE TECHNOLOGIES CO., LTD, Shenzhen (CN)

(72) Inventors: Qing Lan, Shenzhen (CN); Tianlong Dai, Shenzhen (CN); Shoubao Chen, Shenzhen (CN); Ligen Liu, Shenzhen (CN)

(73) Assignee: SHENZHEN GUANKE TECHNOLOGIES CO., LTD., Shenzhen (CN)

( * ) Notice: Subject to any disclaimer, the term of this patent is extended or adjusted under 35 U.S.C. 154(b) by 235 days.

(21) Appl. No.: 17/093,939

(22) Filed: Nov. 10, 2020

(65) Prior Publication Data

US 2022/0111084 A1    Apr. 14, 2022

(30) Foreign Application Priority Data

Oct. 9, 2020   (CN) .......................... 2020110745942

(51) Int. Cl.
  *A61L 2/10*   (2006.01)
  *A61L 2/26*   (2006.01)
(52) U.S. Cl.
  CPC ......... *A61L 2/10* (2013.01); *A61L 2/26* (2013.01); *A61L 2202/11* (2013.01); *A61L 2202/121* (2013.01)

(58) Field of Classification Search
  CPC .......... A61L 2/10; A61L 2/26; A61L 2202/11; A61L 2202/121
  See application file for complete search history.

(56) References Cited

U.S. PATENT DOCUMENTS

2018/0299117 A1* 10/2018 Min ........................ F24F 13/06
2018/0347574 A1* 12/2018 Niemiec ............... F04D 29/545

* cited by examiner

*Primary Examiner* — Sean E Conley
(74) *Attorney, Agent, or Firm* — Maier & Maier, PLLC

(57) ABSTRACT

A UV germicidal panel light for sterilization. The UV germicidal panel light includes a light body in a square shape and with four lateral faces provided with an accommodating groove; four gratings connecting to the light body respectively and provided in four the accommodating grooves respectively, including several light emitting grooves which extend from the end where the gratings are nearby the light body to the end where the gratings are far from the light body and whose inner wall is provided with a light absorption layer; and four UV germicidal modules connecting to the light body or the gratings, with the light emitting direction pointing to the corresponding the grating. The UV germicidal panel light can be applied in occasions with people, can prevent UV rays generated acting on human body and can guarantee the safety and high sterilization efficiency of the UV germicidal panel light.

12 Claims, 7 Drawing Sheets

UV GERMICIDAL PANEL LIGHT

CROSS-REFERENCE TO RELATED APPLICATIONS

The present patent application claims benefit and priority to Chinese Application No. 2020110745942 filed on Oct. 9, 2020 which is hereby incorporated by reference into the present disclosure.

FIELD

The present invention relates to the technical field of a germicidal device, particularly to a UV germicidal panel light.

Background UV lights are of good sterilization effect, but usually require that there are no people in the sterilization occasion, otherwise they will do harm to the human body. To guarantee the body safety, UV lights can be designed with a human body sensing and control device, guaranteeing that UV lights stop working when there are people in the sterilization space; UV lights can also be provided in a sealed cavity, air is inhaled into the sealed cavity via a fan and then is discharged after UV sterilization to finish sterilization. The safety of the former scheme depends on the precision and stability of the sensing and control device, and when there are people in the sterilization occasion for a long time, the sterilization mode of the UV light is hard to enabled, affecting normal use; the latter scheme needs a fan to inhale air into a sealed cavity for sterilization, the sterilization effect relates to the fan's power and the air circulation capacity, this scheme is of high energy consumption and is likely to generate loud noises, and UV rays cannot directly irradiate into the open sterilization occasion outside the UV light, so the sterilization effect of this scheme is much worse than that achieved when the UV light is directly exposed to the sterilization occasion.

The foregoing content is only used for assisting in understanding the technical scheme of the invention, but not means the acknowledgement of that the above content is the current technology.

SUMMARY

To solve deficiencies of existing technologies, the embodiment of the present invention provides a UV germicidal panel light which can be applied in occasions with people and can prevent UV rays generated acting on human body, achieving both safety and high sterilization efficiency of the UV germicidal panel light.

To realize the above subjective, the embodiment of the prevent invention provides a UV germicidal panel light, comprising:

a light body in a square shape and with four lateral faces provided with an accommodating groove;

four gratings connecting to the light body respectively and provided in four the accommodating grooves respectively, comprising several light emitting grooves which extend from the end where the gratings are nearby the light body to the end where the gratings are far from the light body and whose inner wall is provided with a light absorption layer; and four UV germicidal modules connecting to the light body or the gratings, with the light emitting direction pointing to the corresponding grating.

Optionally, the light body comprises a top plate, a bottom plate and erection columns, the top plate and the bottom plate are provided face to face to form a cavity between the top plate and the bottom plate, four the erection columns are provided in four top corners of the cavity respectively, and two ends of the erection columns connect to the top plate and the bottom plate respectively.

Optionally, the light emitting groove of each grating is provided horizontally or obliquely upward;

and/or, each the grating comprises several light absorption plates whose surface is provided with the light absorption layer, two adjacent the light absorption plates form the light emitting groove;

and/or, the UV germicidal module comprises a UV light tube and two reflex housings, the light body and the reflex housings enclose each other to form the accommodating groove, the light body comprises the first supporting arm, and the reflex housings connect to the first supporting arm.

Optionally, the light absorption plate comprises several jagged steps which can reflect UV rays and are provided in sequence, the steps include the first reflex surface and the second reflex surface, the first reflex surface is provided by facing the light inlet of the light emitting groove, the second reflex surface is provided between two adjacent the first reflex surfaces, and the area of the first reflex surface is less than that of the second reflex surface.

Optionally, the light body comprises the second supporting arm on which the gratings are provided flexibly.

Optionally, the UV germicidal panel light comprises four second supporting arms which are provided in four top corners of the light body and are covered by a fixed cover respectively, and the fixed cover and the second supporting arm form a cavity.

Optionally, the second supporting arms are provided with the first insertion hole, the gratings are provided with the second insertion hole corresponding to the first insertion hole;

the UV germicidal panel light also comprises fixed pins provided in the first insertion hole and the second insertion hole to lock the gratings.

Optionally, the top of the light body is provided with a sealing cover, there is a preset space between the sealing cover and the top of the light body, and the sealing cover and the light body are connected in a fixed way.

Optionally, each second supporting arm is provided with the first cross arm, each the first cross arm is provided with a U-shaped hole, one end of the U-shaped hole runs through the outside end of the first cross arm, four the U-shaped holes comprise two sets of the U-shaped holes provided symmetrically based on the midperpendicular of the light body and two sets of U-shaped holes have opposite holing directions.

Optionally, the center of the light body is provided with a centrifugal fan whose air inlet faces the bottom of the light body, the light body is provided with an air inlet channel corresponding to the air inlet of the fan, and the fan blows air from the air outlet to the four gratings.

Optionally, a supporting platform is provided inside the light body, the air inlet channel is provided inside the supporting platform, the fan is provided on the supporting platform to make air from the air outlet of the fan be blown to the light emitting groove on the top of the gratings.

Optionally, the bottom of the light body is also provided with a lighting module, there is a preset space between the lighting module and the bottom of the light body, and the lighting module and the light body are connected in a fixed way.

Optionally, the periphery of the bottom of the light body is provided with a deflector which extends towards the lower part of the light body.

Optionally, the air inlet channel can be provided with a dust-free mesh in a removable way.

Optionally, the UV germicidal panel light also comprises a sensor whose sensing port is provided beneath the gratings.

Beneficial Effect of this Present Invention

In the technical scheme of the present invention, gratings are provided on four lateral faces of the square light body, four gratings coordinate respectively with the UV germicidal module inside the sterilization cavity of the light body, by which UV rays generated by the UV germicidal module emit to gratings around the light body, forming a semi-exposed illumination structure. The UV germicidal panel light is usually hung or directly installed onto the ceiling plate to prevent UV rays irradiating onto human body and improve the use safety of the UV germicidal panel light. In addition, with the structure where one end of the light emitting groove of gratings is far away from the light body, UV rays can directly irradiate in the environment outside the light, which can improve the air sterilization effect in the surrounding environment of gratings. UV rays directly irradiate areas corresponding to four gratings, which can improve the air sterilization scope of UV rays in the use environment. In the meanwhile, under the action of air convection, sterilized air can be exhausted and unsterilized air can be blown into the sterilization area directly irradiated by UV rays as soon as possible to improve the sterilization efficiency of the whole space. In another aspect, gratings are provided with several light emitting grooves which extend from the end where gratings are near from the light body to the other end where gratings are far from the light body. In other words, light emitting grooves of gratings are of long coverage length, the surface of light emitting grooves is provided with a light absorption layer for absorbing UV rays, when UV rays irradiate onto gratings, only UV rays parallel to the inner wall of light emitting grooves can get out of the light, and other UV rays will be absorbed by the inner wall of light emitting grooves, reducing the probability of direct exposure of UV rays to human body and enhancing the use safety of the UV germicidal panel light. In conclusion, the UV germicidal panel light of the present invention can improve the safety of UV sterilization and the sterilization efficiency.

BRIEF DESCRIPTION OF THE DRAWINGS

Drawings are included in the DESCRIPTION and constitute one part of the description, show embodiments of the present invention and are used together with the DESCRIPTION to explain the principle of the present invention.

To describe embodiments of the present invention or technical schemes of existing technologies more clearly, drawings used in descriptions of embodiments or existing technologies are introduced briefly. Obviously, ordinary technicians of the field can access other drawings based on these drawings without making additional creative endeavors. Wherein.

DETAILED DESCRIPTION OF THE EMBODIMENTS

Figure 1:
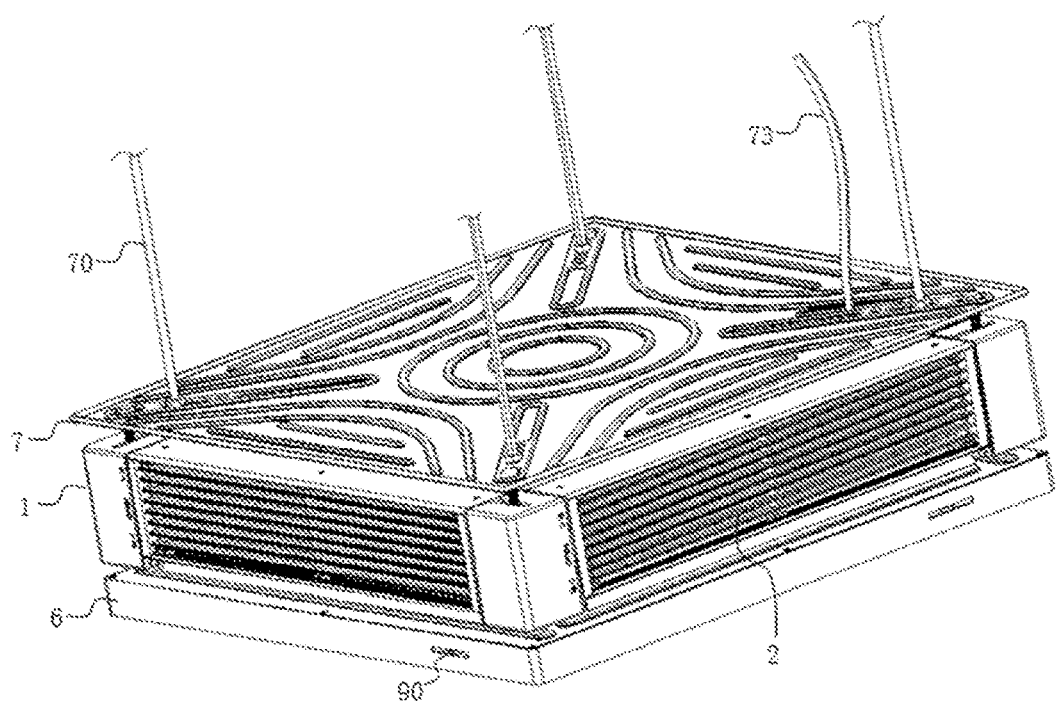
FIG. 1 is the schematic diagram showing the structure of the UV light of an embodiment of the present invention.

In order to make the objects, technical solutions and advantages of this invention more comprehensible, the technical solutions in the embodiments of this invention will be further described in detail below with reference to the drawings. Obviously, the described embodiments are part of the embodiments of this invention and not all of them. Based on the embodiment for the invention, all other embodiments acquired by the ordinary technicians in this field without creative endeavors, shall be in the protection scope of the invention.

The invention is further described in details combined with the following attached figures and specific implementation methods:

Please refer to FIG. 1-FIG. 12. This embodiment of the present invention discloses a UV germicidal panel light which mainly comprises light body 1, four gratings 2 and four UV germicidal modules 3. Light body 1 is in a square shape, four lateral faces of light body 1 are provided with an accommodating groove, four gratings 2 connect to light body 1 respectively and are in four accommodating grooves respectively, gratings 2 include several light emitting grooves 20, light emitting grooves 20 extend from the end where gratings are nearby light body 1 to the end where the gratings 2 are far from light body 1, the inner wall of light emitting grooves 20 is provided with a light absorption layer 21, four UV germicidal modules 3 connect to light body 1 or gratings 2, and the light emitting direction of UV germicidal modules 3 points to the corresponding grating 2.

During working of the light, four UV germicidal modules 3 in light body 1 generate UV rays respectively, UV rays are emitted to the corresponding grating 2 respectively, get out of the light emitting groove 20 of grating 2 and irradiate to the surrounding environment of the light body 1, forming a semi-exposed illumination structure. The UV germicidal panel light is usually hung or directly installed onto the ceiling plate to prevent UV rays irradiating onto human body and improve the use safety of the UV germicidal panel light. In addition, with the structure where one end of the light emitting groove 20 of gratings 2 is far away from the light body 1, UV rays can directly irradiate in the environment outside the light body 1, which can improve the air sterilization effect in the surrounding environment of gratings 2.

UV rays directly irradiate areas corresponding to four gratings 2, which can improve the air sterilization scope of UV rays in the use environment. In the meanwhile, under the action of air convection, sterilized air can be exhausted and unsterilized air can be blown into the sterilization area directly irradiated by UV rays as soon as possible to improve the sterilization efficiency of the whole space. Light emitting grooves 20 of gratings 2 extend from the end where gratings 2 are near from the light body 1 to the other end where gratings 2 are far from the light body 1. In other words, light emitting grooves 20 of gratings 2 are of long coverage length, the surface of light emitting grooves 20 is provided with a light absorption layer 21 for absorbing UV rays, only UV rays parallel to the inner wall of light emitting grooves 20 can get out of the light, and other UV rays will be absorbed by the inner wall of light emitting grooves 21, reducing the probability of direct exposure of UV rays to human body and enhancing the use safety of the UV germicidal panel light. Therefore, the UV germicidal panel light of the embodiment of the present invention can improve the safety of UV sterilization and the sterilization efficiency.

Figure 2:
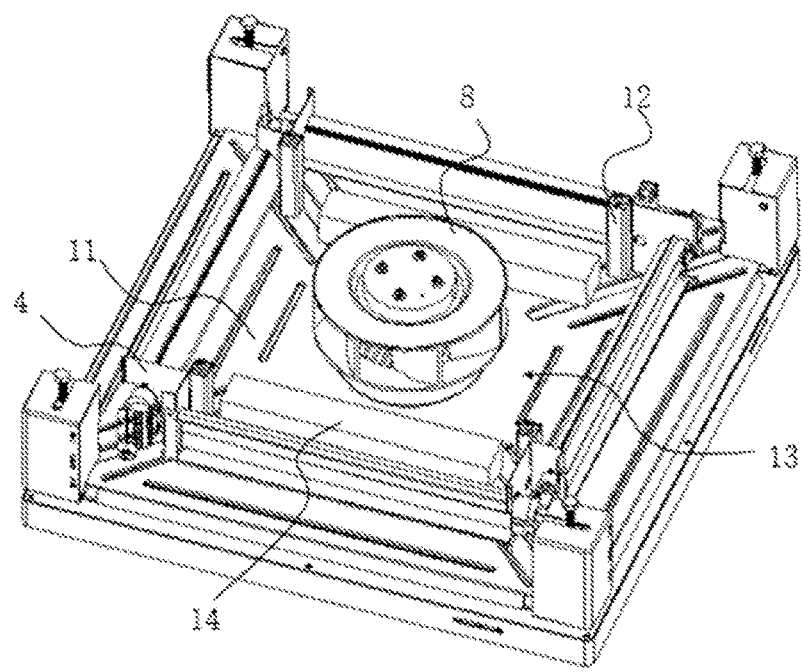
FIG. 2 is the schematic diagram showing the internal structure of the light body of an embodiment of the present invention.
Figure 3:
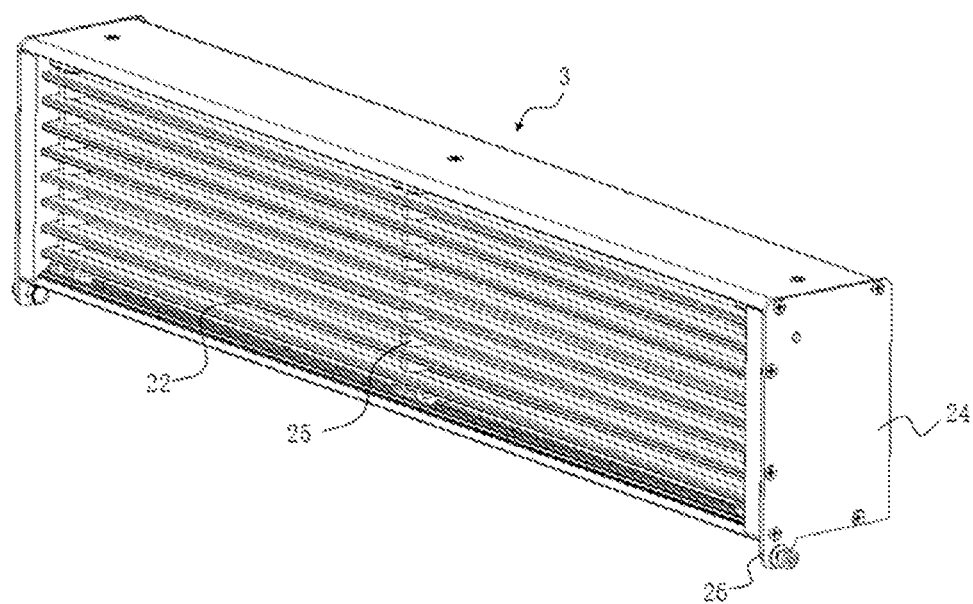
FIG. 3 is the schematic diagram showing the structure of the gratings of an embodiment of the present invention.
Figure 4:
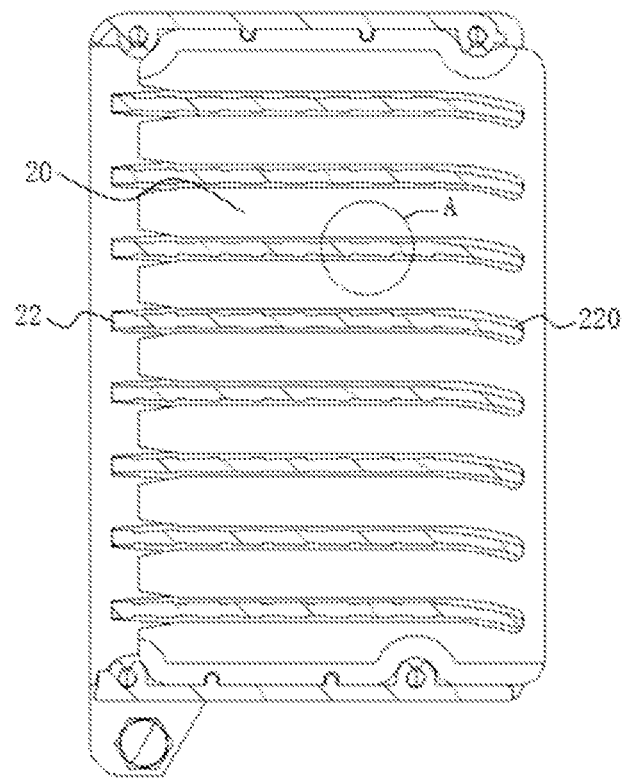
FIG. 4 is the schematic diagram showing the cross-section structure of the gratings of an embodiment of the present invention.
Figure 5:
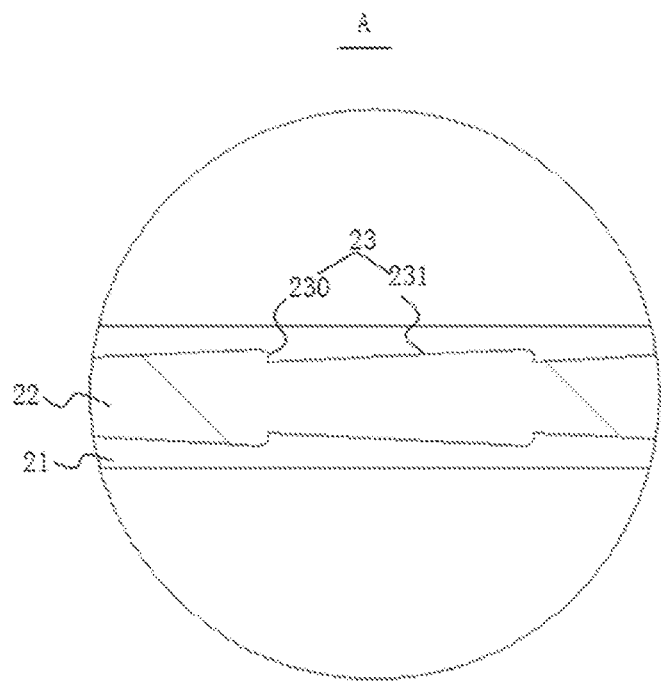
FIG. 5 is the schematic diagram showing the partial enlarged structure at the position A.

According to one embodiment of the present invention, as shown in FIG. 2, light body 1 comprises top plate 10 (FIG. 7), bottom plate 11 and erection column 12, top plate 10 and bottom plate 11 are provided face to face to form a cavity 13 between top plate 10 and bottom plate 11, four erection columns 12 are provided in four top corners of cavity 13 respectively, and two ends of erection columns 12 connect to top plate 10 and bottom plate 11 respectively. When sterilizing air, the inside of light body 1 and the sterilization environment form air convection which can promote quick exchange of air in the sterilized area and unsterilized area. In this embodiment, light body 1 adopts a simple structure, so that the cavity 13 between the top plate 10 and the bottom plate 11 can be as large as possible, reducing wind drag.

According to one embodiment of the present invention, light body 1 is also provided with power supply 14 inside, power supply 14 is an integral module used for driving electronic devices in light body 1 to work. Wherein, power supply 14 comprises: a UV module power supply for driving UV module 2 to work, fan power supply for driving the fan to work and drive power supply for driving the control system circuit of light body 1 to work.

According to one embodiment of the present invention, the light emitting groove 20 of each grating 2 is provided horizontally or obliquely upward. When light emitting grooves 20 are provided horizontally, UV rays horizontally irradiate into the external environment of light body 1 through light emitting grooves 20. When light emitting grooves 20 are provided obliquely upward, UV rays irradiate into the external environment of light body 1 obliquely upward through light emitting grooves 20. The panel light is hung or directly installed onto the ceiling; preventing UV rays out from gratings 2 irradiating onto human body.

According to one embodiment of the present invention, each grating 2 comprises several light absorption plates 22, the surface of light absorption plates are provided with a light absorption layer 21, and a light emitting groove 20 is formed between two adjacent light absorption plates 22. Some UV rays from light emitting grooves 20 are not parallel to the light emitting direction of light emitting grooves 20, such unnecessary UV rays irradiate onto light absorption plates 22 first and then are absorbed by light absorption layer 21 on the surface of light absorption plates 22, preventing such UV rays irradiating into the outside.

Light absorption plate 22 comprises several jagged steps 23 which can reflect UV rays and are provided in sequence, steps 23 include the first reflex surface 230 and the second reflex surface 231, the first reflex surface 230 is provided by facing the light inlet of the light emitting grooves 20, the second reflex surface 231 is provided between two adjacent the first reflex surfaces 230, and the area of the first reflex surface 230 is less than that of the second reflex surface 231. During work, when some unnecessary UV rays from light emitting grooves 20 irradiate onto light absorption plates 22, some of them are absorbed by the light absorption layer 21, unnecessary UV rays which cannot be absorbed by the light absorption layer 21 irradiate onto the first reflex surface 230 first and are reflexed by the first reflex surface 230, and then the irradiating direction of such unnecessary UV rays will not face light outlet of light emitting grooves 20 and will face the light inlet of light emitting grooves 20, such unnecessary UV rays will irradiate onto the second reflex surface 231 and then are reflexed on several second reflex surfaces 231 inside light emitting grooves 20 in sequence. During this process, after several times of absorption of the light absorption layer 21, such unnecessary UV rays will be absorbed. So, this can effectively reduce the proportion of unnecessary UV rays out of gratings 2 and improve the safety of UV germicidal panel light.

In one concrete embodiment, the first reflex surface 230 is provided as a vertical surface which is vertical to the light emitting direction of light emitting grooves 20, or provided as an inclined surface which is inclined to the light inlet of light emitting grooves 20. When the first reflex surface 230 is a vertical surface vertical to the light emitting direction of light emitting grooves 20, the first reflex surface 230 can absorb more unnecessary UV rays inside light emitting grooves. After reflex of the first reflex surface 230, such unnecessary UV rays will not irradiate from the light outlet of light emitting grooves 20 but the light inlet of light emitting grooves 20, preventing such rays irradiating into the outside through the light outlet; When the first reflex surface 230 is an inclined surface which is inclined to the light inlet direction, although a small number of unnecessary UV rays are received by the first reflex surface 230, it can better coordinate with the second reflex surface 231 at this angle, after reflex of the first reflex surface 230, UV rays irradiate onto the second reflex surface 231 and then are reflexed on the upper inner wall and the lower inner wall of light emitting grooves 3 to promote absorption of UV rays by the light absorption layer 21.

In one concrete embodiment, the top of the first reflex surface 230 is provided with a circular chamfer.

In one concrete embodiment, the second reflex surface 231 can be provided as a plane or concave surface optionally. The second reflex surface 231 is gradually inclined to one side of light emitting grooves 20 along the light emitting direction.

In one concrete embodiment, the light absorption plate 22 is provided with a light guide part 220 on one end of the light inlet of light emitting grooves 20, and the light guide part 220 can be a declivitous inclined surface or arc surface optionally. The light guide part 220 is used for guiding unnecessary UV rays to irradiate onto the upper side and the lower side of light emitting grooves 20, so that the light absorption plate 22 can absorb such unnecessary UV rays or reflex them into the light inlet.

According to one embodiment of the present invention, the grating device also comprises the supporting frame component which mainly includes a pair of top plates 24 and clamping parts 25, one pair of end plates 24 are face to face, several light absorption plates 21 are between one pair of end plates 24, and several light absorption plates 21 are clamped by the clamping part 25 to form a light emitting groove 20 with a preset light emitting direction between two adjacent light absorption plates 21.

According to one embodiment of the present invention, the end plate 24 has a mounting arm 26 extending to the bottom; the mounting arm 26 is used to install the grating device. For example, with the help of the mounting arm 26, the grating device is installed onto the UV light. Optionally, the mounting arm 26 can be installed onto the UV in a removable (rotatable or slidable) way.

Figure 6:
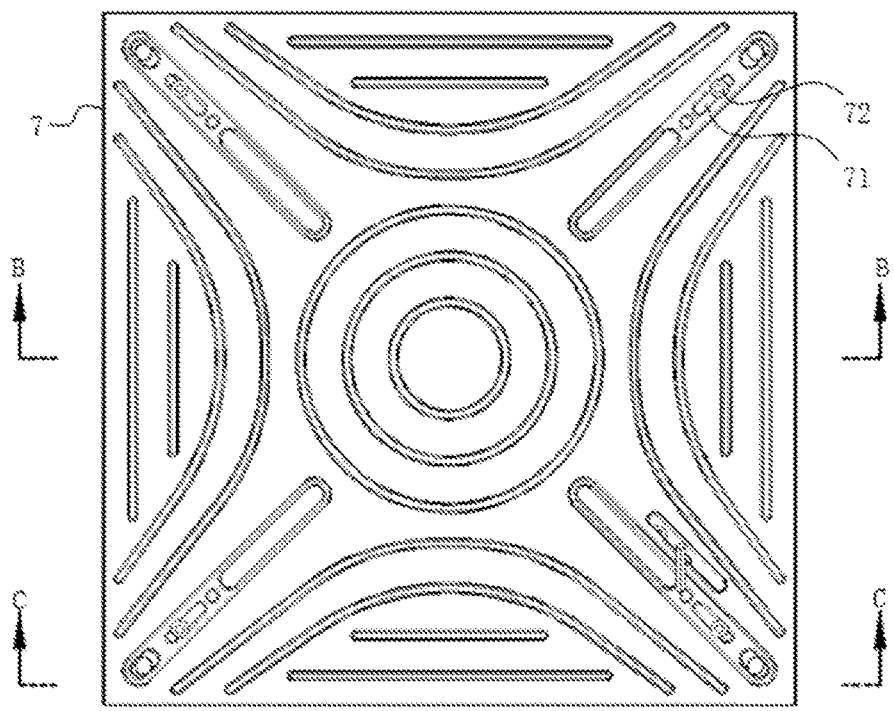
FIG. 6 is the top view showing the UV light of an embodiment of the present invention.
Figure 7:
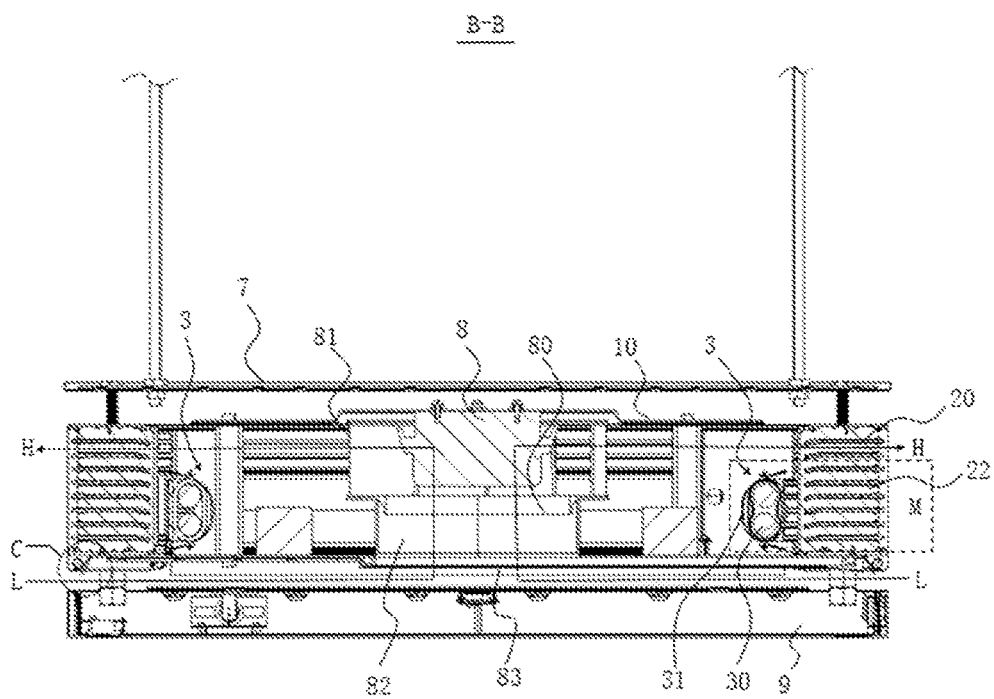
FIG. 7 is the schematic diagram of the cross section B-B.
Figure 8:
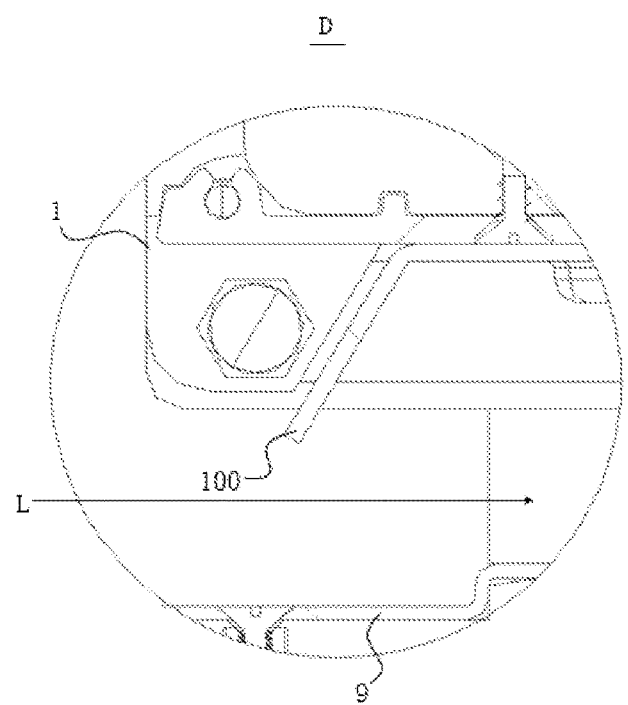
FIG. 8 is the schematic diagram showing the partial enlarged structure at the position D.
Figure 9:
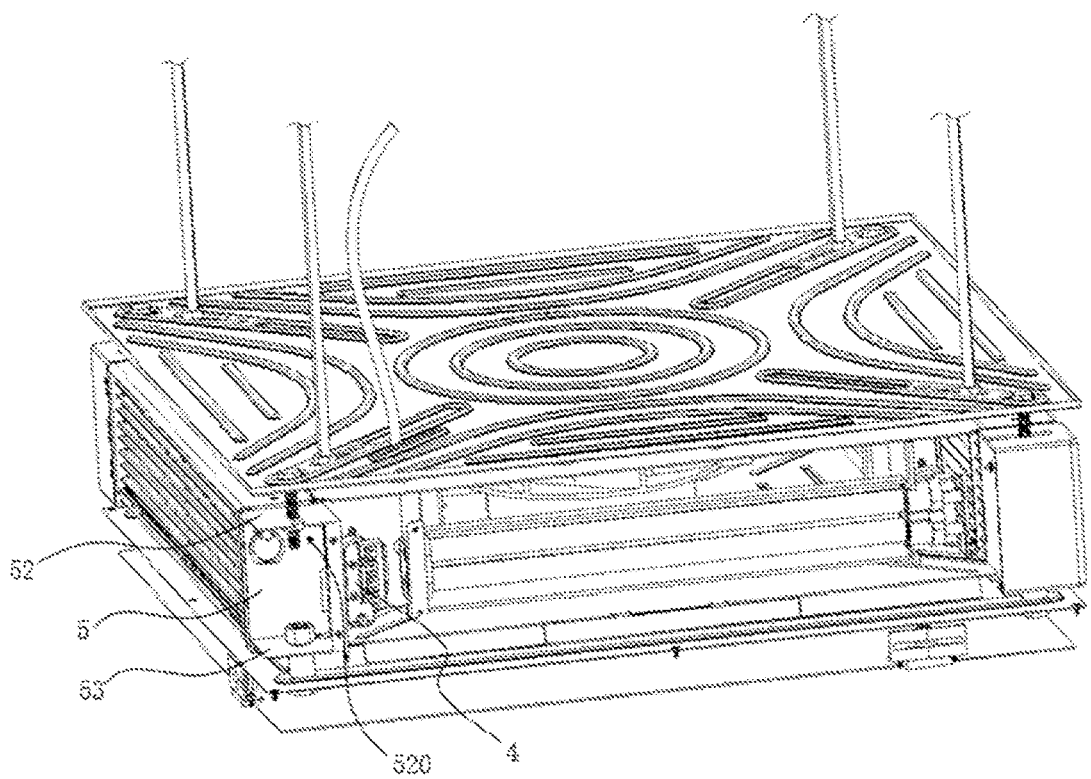
FIG. 9 is the schematic diagram showing the structure of the UV light of an embodiment of the present invention from another aspect of gratings.
Figure 10:
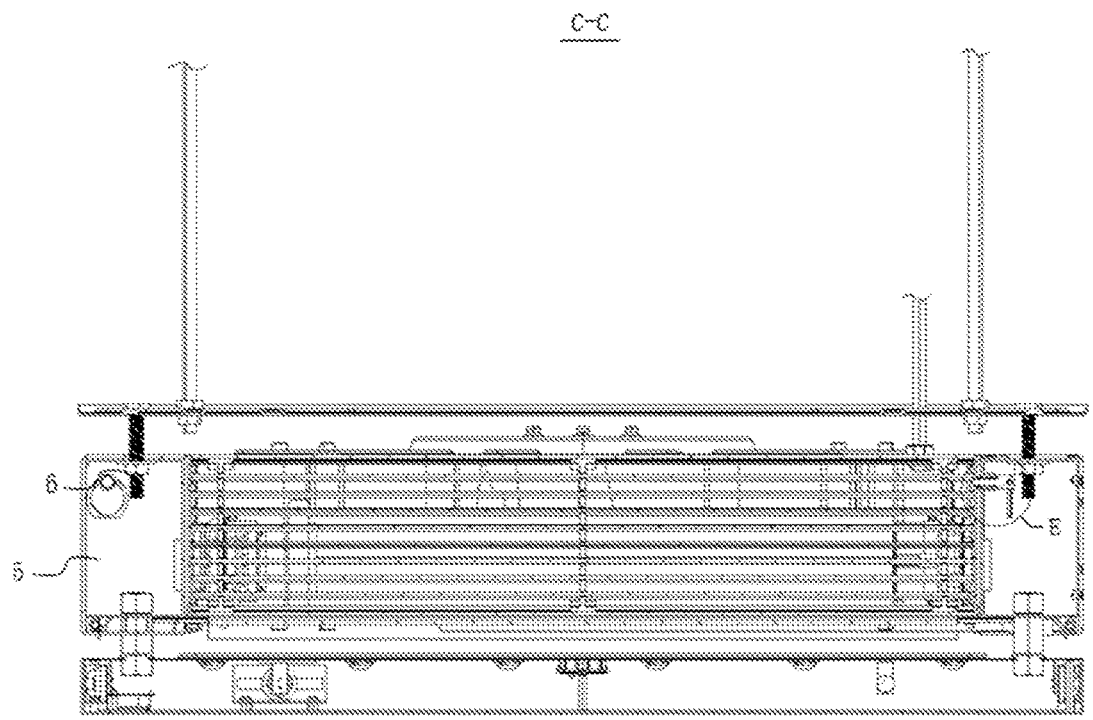
FIG. 10 is the schematic diagram showing the partial enlarged structure at the position E.

According to one embodiment of the present invention, as shown in FIG. 6 and FIG. 7, the UV module 3 comprises the UV light tube 30 and reflex housing 31, light body 1 and reflex housing 31 enclose each other to form the aforesaid accommodating groove, light body 1 comprises the first supporting arm 4, reflex housing 31 connects to the first supporting arm 4, and the UV light tube 30 is provided between the reflex housing 31 and the grating 2. Some of UV rays generated by the UV light tube 30 directly irradiate onto gratings 2, others irradiate onto reflex housing 31 and are reflexed onto gratings 2 by reflex housing 31 to improve the use ratio of UV rays.

In one concrete embodiment, the first supporting arm 4 is on the end shared by two adjacent UV modules 3, the first supporting arm 4 is in an L shape, one free arm of the first supporting arm 4 connects to the end of one reflex housing 31, the other free arm of the first supporting arm 4 connects to the end of the other reflex housing 31.

According to one embodiment of the present invention, light body 1 also comprises the second supporting arm 5, and gratings 2 are provided on the second supporting arm 5 in a movable way. For example, the second supporting arm 5 is provided with a slide slot or slide rail, gratings 2 can be provided in this slide slot or slide rail in a movable way to realize relative motion between gratings 2 and the second supporting arm 5; or, gratings 2 connect to the second supporting arm 5 in a movable way.

Specifically, there are four second supporting arms 5 which are provided in four top corners of light body 1 and are covered with a fixed cover 50 respectively, and a fixed cover 50 and a second supporting arm 5 form a cavity.

In one concrete embodiment, the second supporting arm 5 is provided with the first insertion hole 51, gratings 2 are provided with the second insertion hole 27 corresponding to the first insertion hole 51, the UV germicidal panel light also comprises fixed pins 6 which pass through the first insertion hole 51 and the second insertion hole 27 to attach gratings 2. Wherein, fixed pins 6 can be a structure which can move along the first insertion hole 51 and the second insertion hole 27, when fixed pins 6 get out of the second insertion hole 27, that is the attachment between gratings 2 and the second supporting arm 5 is cancelled, gratings 2 can be provided on the second supporting arm 5 in a movable way. Optionally, the upper end of gratings 2 connects to the second supporting arm 5 through a fixed pin 6, the lower end of gratings 2 connects to the second supporting arm 5 through the mounting arm 26. For example, mounting arm 26 can connect to the second supporting arm 5 in a rotatable way. So, when fixed pins 6 get out of the second insertion hole 27, gratings 2 can realize rotation relative to the second supporting arm 5 by taking the connection position of mounting arm 26 and the second supporting arm 5 as the rotation axis. When maintaining the light, the operator should rotate gratings 2 first to make the UV module 3 inside the light body 1 exposed, so that the UV module can be maintained conveniently.

Figure 11:
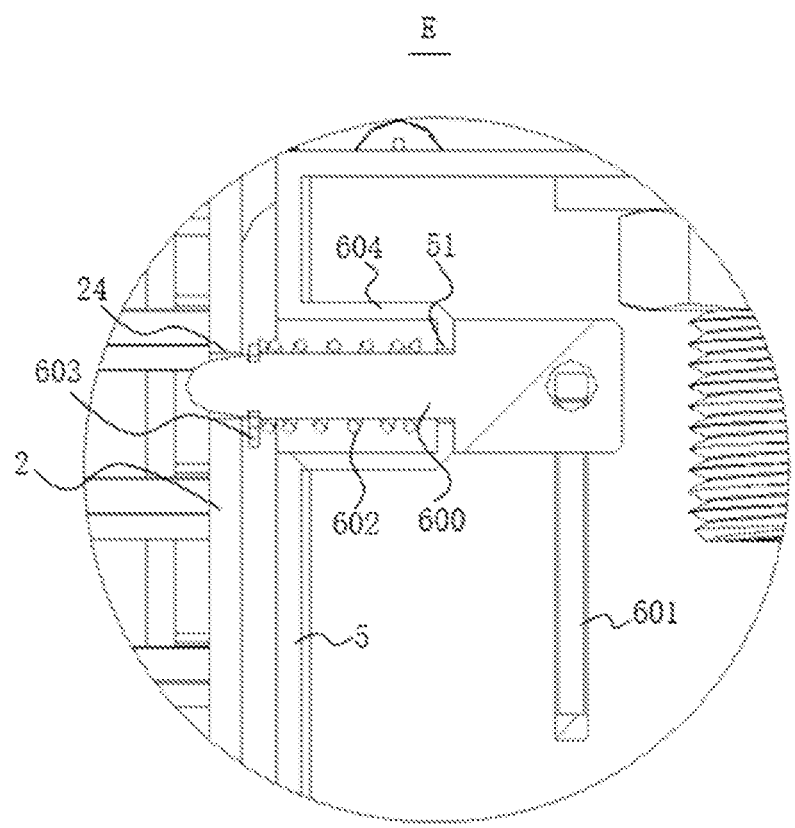
FIG. 11 is the schematic diagram of the cross section C-C.
Figure 12:
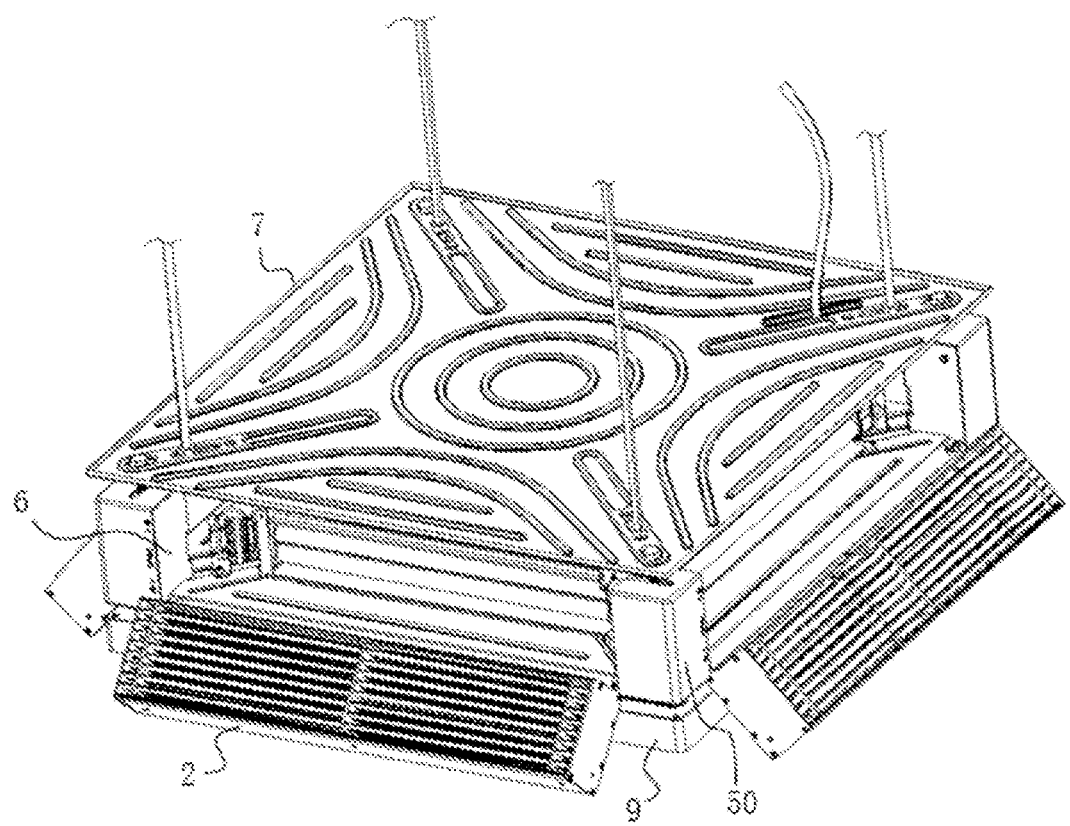
FIG. 12 is the schematic diagram showing the structure of UV light of an embodiment of the present invention after removing partial shell.

Please refer to FIG. 11. Fixed pins 6 mainly comprise: pin shaft 600, pull ring 601, elastic part 602 and snap ring 603. Pin shaft 600 passes through the first insertion hole 51 and the second insertion hole 27, pull ring 601 is on one side of the second supporting arm 5 apart from grating 3, pull ring 601 connects to pin shaft 600, elastic part 602 and snap ring 603 are provided on pin shaft 600, one end of elastic part 602 is against the second supporting arm 5, the other end of the elastic part 602 connects to the snap ring 603, and snap ring 603 is against grating 3.

According to the above embodiment, when grating 3 is closed, the front end of pin shaft 600 is embedded in the second insertion hole 27, elastic part 602 is under the normal state or small compression, grating 3 is restricted by pin shaft 600 and cannot realize rotation relative to the second supporting arm 5; when grating 3 is open, pull ring 601 is pulled away from grating 3 to drive pin shaft 600 to move together with pull ring 601 along the axis direction, until the end of pin shaft 600 get out of the second insertion hole 27 and grating 3 is not restricted by pin shaft 600 and can realize rotation relative to the second supporting arm 5, in such a case, elastic part 602 is under great compression, when grating 3 rotates to the closed position from the open position, under the action of elastic part 602, pin shaft 600 automatically returns to the initial position, that is, the front end of pin shaft 600 stretches into the second insertion hole 27 and restricts the rotation of grating 3 again.

Optionally, the front end of pin shaft 600 can be a spherical structure, so that it can guide the direction when the front end of pin shaft 600 stretches into the second insertion hole 27; one lateral surface of the second supporting arm 5 apart from grating 3 can be provided with shaft sleeve 604 optionally, shaft sleeve 604 is provided by sharing the same axis with the first insertion hole 51, when grating 3 is closed, pin shaft 600 passes through shaft sleeve 604 and the first insertion hole 51 in sequence and stretches into the second insertion hole 27, and shaft sleeve 604 guides direction for motion of pin shaft 600 to realize straight motion of pin shaft 600 along the axis direction.

According to one embodiment of the present invention, as shown in FIG. 1 and FIG. 6, the top of light body 1 is provided with a sealing cover 7, there is a preset space between sealing cover 7 and light body 1, and sealing cover 7 connects to light body in a fixed way. Optionally, sealing cover 7 can realize fixed connection to light body 1 through a bolt structure. Sealing cover 7 can be hung onto ceiling like the embedded panel light, restricting that the light only sterilizes air under the ceiling.

Sealing cover 7 is installed with a fixed rod 70 which is used to fasten the light onto the ceiling when installing the light. Wherein, sealing cover 7 is provided with mounting holes 71, and one end of fixed rod 70 is installed to sealing cover 7 through an mounting hole 71. Preferentially, four fixed rods 70 and four mounting holes 71 are provided, four fixed rods 70 and mounting holes 71 are provided in four diagonal corners of sealing cover 7 respectively, mounting holes 71 are in a rectangular shape, the extension line of the length direction of mounting holes 71 passes the center of sealing cover 7, when fixed rods 70 are provided on sealing cover 7 in a fixed way, the relative position between fixed rods 70 and sealing cover 7 in the mounting hole 71 can be adjusted, so that fixed rods 70 can be adjustable when they are installed and fixed, fixed rods 70 can be fixed to sealing cover 7 with one pair of nuts 72, fixed rods 70 are provided with threads, one pair of nuts 72 are on both sides of sealing cover 7 respectively, one pair of nuts 72 work with fixed rods 70 and then fasten fixed rods 70 onto sealing cover 7 through mutual tightening.

UV germicidal panel light also comprises power cord 73, one end of power cord 73 connects electrically to electrical components inside light body 1, power cord 73 is led to the upper end of sealing cover 7 through sealing cover 7, and when installing the light, power cord 73 connects to indoor power supply circuit to provide power for the light.

In one concrete embodiment, the upper end of each second supporting arm 5 is provided with a first cross arm 52, each first cross arm 52 is provided with a U-shaped hole 520, one end of the U-shaped hole passes through the outside end of the first cross arm 52, four U-shaped 520 comprises two groups of U-shaped 520 provided symmetrically based on the midperpendicular of light body 1, and two groups of U-shaped holes 520 have opposite holing directions. When installing sealing cover 7 and light body 1, sealing cover 7 should be installed first, and then bolts should be installed to sealing cover 7, and finally light body 1 clips into the bolt structure along U-shaped hole 520 and the tightness is adjusted.

According to one embodiment of the present invention, the center of light body 1 is provided with a centrifugal fan 8, the air inlet 80 of fan 8 faces the bottom of light body 1, light body 1 is provided with an air inlet channel corresponding to the air outlet 81 of the fan, and the air outlet 81 of fan 8 blows air to four gratings 2. Fan 8 mainly has the following functions: promote indoor air circulation, especially for circulation of air in the area irradiated by UV rays and air in other areas, and during working, UV rays generated by UV module 3 sterilize indoor air to improve the sterilization efficiency.

According to one embodiment of the present invention, light body 1 is provided with a supporting platform 82 inside, the air inlet channel is provided inside supporting platform 82, fan 8 is provided on supporting platform 82 to make air outlet 81 of fan 8 blow outlet airs to light emitting grooves 20 on top of gratings 2. In each preferential embodiment, the air inlet channel is provided with dust-free mesh 83, when fan 8 works, external air flows into fan 8 through the air inlet channel, dust-free mesh can filter dust in air flowing into the air inlet channel and fan 8 to purify air, and dust-free mesh 83 can be provided in the air inlet channel in a removable way, so that dust-free mesh 83 can be replaced conveniently.

According to one embodiment of the present invention, the bottom of light body 1 is also provided with lighting module 9, there is a preset space between lighting module 9 and the bottom of light body 1, and the lighting module 9 connects to light body 1 in a fixed way. During working, UV germicidal module 3 in light body 1 irradiates UV rays into the surrounding environment of light body 1 through gratings 2 to sterilize and disinfect indoor air, lighting module 9 can serve as the indoor light source and connect to light body 1 via a bolt structure to form a preset space between lighting module 9 and light body 1, this preset space can guarantee that air at the bottom of light body 1 flows into fan 8 via the air inlet channel to realize circulation of air inside and outside light body 1.

Optionally, the lower part of the second supporting arm 5 is also provided with the second cross arm 53, the lighting module 9 and the second cross arm 53 are connected through a bolt structure, the second supporting arm 5 is in four top corners of light body 1 and the fixed cover 50 on the second supporting arm 5 is removable, so lighting module 9 can be disassembled conveniently after fixed cover 50 is removed.

According to one embodiment of the present invention, the bottom periphery of light body 1 is provided with a deflector 100 which extends towards the lower part of deflector 100, and preferentially deflector 100 gradually inclines downward towards the direction apart from light body 1. The design of deflector 100 is conducive to increasing the proportion of air inhaled into the cavity of fan 8 at the bottom of light body 1 and reducing the proportion of air inhaled into fan 8 in the sterilization area, promoting exchange and circulation of sterilized air and unsterilized air and improving the whole sterilization efficiency.

In one concrete embodiment, UV module 3 is at the height H, air outlet 81 is at the height M, the air inlet area at the bottom of light body 1 is at the height L. Air outlet 81 is the upmost, the air inlet area at the bottom of light body 1 is the lowest, the height M of UV module 3 separates the height M of air outlet 81 and height L of air inlet area at the bottom of light body 1. So, sterilized air in the area corresponding to height H can exchange with air in the area corresponding to height M and height L and air in light body 1 can circulate more smoothly, reducing airflow disturbance and reducing noises generated by the system.

According to one embodiment of the present invention, the UV germicidal panel light also comprises a sensor 90 whose sensing port is provided beneath grating 2. Sensor 90 is used to detect whether there are people in the area where is irradiated by UV rays from the UV germicidal panel light. For example, when the roof is repaired, there will be people who conduct high-place operation indoors, so it will do harm to the operator if UV rays irradiates into the outside of light body 1 in such a case, and the existence of sensor 90 can detect high-place operation personnel in real time, so that the UV germicidal module can stop working. Control components used for controlling the UV germicidal module to stop working can be conventional control device or circuits in this field, for which no more details are described in the DESCRIPTION of the present invention.

In one concrete embodiment, sensor 90 is provided on the lateral face of lighting module 9. Preferentially, sensor 90 is provided on each lateral face of lighting module 9 to ensure the accuracy of the detection result.

In the description of the present invention, it is to be explained that the terms "upper", "lower", and other presentations relating to orientation or positional relationship is based on the orientation or positional relationship shown in the drawings, and is merely for the convenience of the description of the invention or a simplified description, rather than indicating or implying that the device or component referred to having a specific orientation or being manufactured or operated in a specific orientation, which shall not be construed as limitations on the invention. In addition, term "first" and "second" are only used for description and cannot be understood as the indication or implication of relative importance.

In the description of the present invention, it shall be noted that, unless otherwise clearly specified and limited, the terms "installation", "joint" or "connection" shall be understood in a broad sense, for example, it can be a fixed connection or a detachable connection or all-in-one connection; mechanical connection or electrical connection; Direct jointing or indirect jointing via a medium or jointing between the inside of two components. As to ordinary technical personnel in the field, they can understand the concrete meaning of the terms in the present invention in accordance with the specific situations. In addition, in the description of the present invention, "several" means two or more, unless otherwise specified.

The above are only the preferred embodiments of the present invention, and are not intended to limit the present invention. Any modifications, equivalent substitutions and improvements made within the spirits and principles of the present invention shall be included in the protection scope of the present invention.

What is claimed is:

1. A UV germicidal panel light comprising:
a light body having a square shape with four lateral faces, each of the four lateral faces provided with an accommodating groove;
four gratings connected to the light body, wherein each of the four gratings are provided in a corresponding one of the accommodating grooves and each of the four gratings comprise several light emitting grooves and an inner wall provided with a light absorption layer, the several light emitting grooves extending towards and away from the light body; and
four UV germicidal modules connected to the light body or the gratings wherein each of the four UV germicidal modules are directed towards a corresponding one of the four gratings.

2. The UV germicidal panel light as claimed in claim 1, wherein the light body comprises a top plate, a bottom plate and erection columns, the top plate and the bottom plate are provided face to face to form a cavity between the top plate and the bottom plate, four of the erection columns are provided in four top corners of the cavity respectively, and two ends of the erection columns connect to the top plate and the bottom plate respectively.

3. The UV germicidal panel light as claimed in claim 1, wherein the light emitting groove of each grating is provided horizontally or obliquely upward; and/or
wherein each of the four gratings comprises several light absorption plates whose surface is provided with the light absorption layer, and each of the several light emitting grooves are formed by two adjacent light absorption plates; and/or
wherein each of the four UV germicidal modules comprises a UV light tube and a reflex housing, the light body and the reflex housings forming the accommodating grooves, and the light body comprises a first supporting arm which connects to the reflex housings.

4. The UV germicidal panel light as claimed in claim 3, wherein each of the light absorption plates comprise several jagged steps which reflect UV rays and are provided in sequence,
wherein each of the steps includes a first reflex surface and a second reflex surface,
wherein the first reflex surfaces face an inlet of the light emitting groove and the second reflex surfaces are each provided between two of the first reflex surfaces, and
wherein an area of the first reflex surface is less than that of the second reflex surface.

5. The UV germicidal panel light as claimed in claim 4, wherein the light body comprises a second supporting arm by which the four gratings are movably mounted to the light body.

6. The UV germicidal panel light as claimed in claim 4, wherein the UV germicidal panel light comprises four second supporting arms which are provided in four top corners of the light body and are covered by a fixed cover, and
wherein each fixed cover and a corresponding second supporting arm form a cavity.

7. The UV germicidal panel light as claimed in claim 6, wherein each of the second supporting arms are provided with a first insertion hole, and each of the gratings are provided with a second insertion hole corresponding to one of the first insertion holes; and
wherein the UV germicidal panel light further comprises fixed pins provided in the first insertion holes and the second insertion holes to lock the gratings.

8. The UV germicidal panel light as claimed in claim 6, wherein a top of the light body is provided with a sealing cover fixed to the light body and spaced apart from the light body.

9. The UV germicidal panel light as claimed in claim 8, wherein each of the second supporting arm is provided with a first cross arm and each of the first cross arms is provided with a U-shaped hole, and
wherein one end of the U-shaped hole runs through an outside end of a respective first cross arm.

10. The UV germicidal panel light as claimed in claim 1, wherein a center of the light body is provided with a centrifugal fan whose air inlet faces a bottom of the light body, and
wherein the light body is provided with an air inlet channel corresponding to the air inlet of the centrifugal fan, and the centrifugal fan blows air from an air outlet of the centrifugal fan to the four gratings.

11. The UV germicidal panel light as claimed in claim 1, wherein a bottom of the light body is provided with a lighting module fixed to the light body and spaced apart from the light body.

12. The UV germicidal panel light as claimed in claim 2, wherein a periphery of a bottom of the light body is provided with a deflector which extends towards a lower part of the light body.

* * * * *